United States Patent [19]
Griffith et al.

[11] Patent Number: 4,950,787
[45] Date of Patent: Aug. 21, 1990

[54] CHEMICAL PROCESS

[75] Inventors: Edward J. Griffith, Manchester; Liou-Liang Horng, Creve Coeur; Mark E. Jason, Chesterfield, all of Mo.

[73] Assignee: Monsanto Company, St. Louis, Mo.

[21] Appl. No.: 236,080

[22] Filed: Aug. 24, 1988

[51] Int. Cl.$^5$ .............................................. C07C 59/125
[52] U.S. Cl. ...................................................... 562/583
[58] Field of Search .......................................... 562/583

[56] References Cited

U.S. PATENT DOCUMENTS

| | | | |
|---|---|---|---|
| 3,635,830 | 1/1972 | Lamberti et al. | 252/89 |
| 3,692,685 | 9/1972 | Lamberti et al. | 252/89 |
| 3,914,297 | 10/1975 | Lamberti et al. | 260/535 P |
| 4,663,071 | 5/1987 | Bush et al. | 252/174.19 |
| 4,689,167 | 8/1987 | Collins et al. | 252/95 |

OTHER PUBLICATIONS

Chemical Abstracts, vol. 60, 2295G, 1964.
Chemical Abstracts, vol. 64, 4224G, 1966.

*Primary Examiner*—Bruce Gray
*Attorney, Agent, or Firm*—Raymond C. Loyer; Richard H. Shear; Arnold H. Cole

[57] ABSTRACT

There is disclosed an improved process for preparing 1-hydroxy-3-oxa-1,2,4,5-pentane tetracarboxylic acid and 3,6-dioxa-1,2,4,5,7,8-octane hexacarboxylic acid wherein the unreacted starting acids are recovered in more desirable crystal habit. The acids are precipitated in salt form by lowering the pH of the reaction product to a range of from 4 to below 6 stepwise. The pH is lowered to above 6 in the first step and then relatively rapidly reduced to the desired level in the second step.

26 Claims, No Drawings

CHEMICAL PROCESS

This invention relates to a process for making ether carboxylic acids and more particularly to processes for making ether carboxylates prepared by a calcium ion catalyzed reaction in alkaline medium of maleic acid salt and a carboxylate salt containing a reactive hydroxyl group. Such reactions are of the type typically referred to as Michael condensation reactions.

Polycarboxylic acids have long been known to be useful, usually in the salt form, as detergent builders or sequestrants. Also, ether carboxylates useful as metal sequestering and detergent builders have been known and are most desirable for their beneficial effects in laundering applications.

While many carboxylate compounds in the prior art have utility as a builder or sequesterant in laundry detergent formulations, it has been found that certain ether carboxylates are more attractive and cost effective for such utility. In the field of detergent builders and sequesterants for laundry detergent formulations low cost of the components is extremely important because it is in a very competitive market. While many ether carboxylate compounds have been found to be useful there is needed more economical manufacturing processes whereby such compounds can be economically produced in large volume.

One example of ether carboxylates is a mixture of polycarboxylic acids or salts thereof, particularly the sodium salts, of 1-hydroxy-3-oxa-1,2,4,5-pentane tetracarboxylic acid (HOPTC) and 3,6-dioxa-1,2,4,5,7,8-octane hexacarboxylic acid (DOOHC) which is highly useful in detergent formulations as a sequesterant or builder. This mixture is prepared by reaction of a combination of D,L-tartrate salts with maleate salts catalyzed by calcium ions. Due to equilibria present in the reaction and to the need for the presence of particular reactant ratios to obtain particularly preferred ratios of HOPTC and DOOHC in the product, there is considerable unreacted D,L-tartrate and maleate present at the end of the condensation reaction. Further, to provide a more economical process it is desired that a means be found to economically recover and reuse the unreacted D,L-tartrate and maleate rather than merely discharging maleate and tartrate as waste.

SUMMARY OF THE INVENTION

In accordance with this invention, there is provided a process for preparing HOPTC and DOOHC by the reaction of the salts of maleic acid and a tartaric acid said reaction catalyzed by calcium ions and conducted under alkaline conditions wherein unreacted salts are conveniently recovered in such manner that they may be recycled to the synthesis reaction to produce additional HOPTC and DOOHC. It has been discovered that at a limited range of acidity certain unreacted salts are conveniently recovered from the reaction mixture at the conclusion of the reaction. By reducing the pH of the reaction mixture to a range within about 4.5 to about 5.5 by combining a suitable acid with the reaction mixture, the insoluble salts of starting acids precipitate while the desired ether carboxylate product remains in solution. The precipitate is removed by known means such as filtration thereby allowing further processing of the ether carboxylate solution.

A process whereby precipitate is produced by stepwise reduction of pH has been discovered wherein the precipitate is provided in improved form. That is, the pH of the crude reaction mixture is reduced to within a range of from about 6.0 to about 9 in the first step and then the pH of the reaction mixture is reduced to the desired range of from about 4.5 to about 5.5 relatively more rapid. It has been found that by the process of this invention the precipitate produced is of sufficient porosity to allow much faster filtration rates and provides a filter cake having less residual free liquid. Because the filter cake contains less free liquid it can be transported more efficiently.

In another aspect of this invention, the calcium ions employed to catalyze the condensation reaction to prepare the ether carboxylate is conveniently recovered and recycled to the synthesis reaction by precipitating the calcium as a calcium carbonate. The precipitation is accomplished by combining the reaction mixture, typically after removal of unreacted starting salts, with an alkaline earth or alkali metal carbonate at a pH in the range of from about 7 to about 12. The precipitate is removed by known means, preferably by filtration.

DETAILED DESCRIPTION OF THE INVENTION

Calcium catalyzed reactions for the production of ether carboxylates are known. A typical example of such a process is disclosed in U.S. Pat. No. 4,663,071 to Bush et al and such patent is hereby incorporated by reference.

The U.S. Patent discloses a process for preparing a mixture of HOPTC and DOOHC referred to above. In such process the mixture is obtained by the reaction of maleic acid and tartaric acid salts. This disclosure is a typical example of the reaction of maleic acid with tartaric acid said reaction being catalyzed by calcium ions and conducted in alkaline medium. Such reactions are known in the art as Michael condensation reactions. It is typical of the Michael condensation reactions to provide the most effective equilibrium state for the production of the desired compound or mixture by control of the reactant ratio.

It has been found that D,L-tartaric acid salts possess different solubility characteristics than do either the D- or L- isomers such that the D,L- isomer conveniently precipitate from solution at a pH in the range of from about 7 to about 9.5 while the calcium salts of HOPTC and DOOHC remain in solution and can be purified for use as a builder combination in detergent formulations.

The recovery of unreacted maleate salts from calcium catalyzed reactions of maleic acid salts with salt of tartrate salts in alkaline medium is conveniently achieved by acidifying the reaction product so as to reduce the pH to within the range of about 4 to below about 6.

A particular advantage of the process of this invention, whereby unreacted maleate salt is recovered, is the ability to regulate the reactant ratio more freely since convenient recovery and recycle is possible. Loss of unreacted maleate salt is insignificant and its recovery economical, particularly when maleic acid is employed to reduce the pH of the reaction product of the condensation reaction.

In accordance with one embodiment of this invention the unreacted D,L-tartrate and maleate starting materials are removed by precipitation from the reaction mass prior to the removal of calcium from the system. Specifically, calcium D,L-tartrate and mono sodium maleate are precipitated from the reaction mixture by adjustment of the pH of the reaction solution in two steps. The precipitate of calcium D,L-tartrate and mono sodium maleate is then returned to a subsequent condensation synthesis reaction. It has been found that the small amounts of by-products such as malate and fumarate and residual amounts of HOPTC and DOOHC trapped in the precipitate are not deleterious to the use of this recycled precipitate in subsequent condensation synthesis reaction.

FORMATION OF HOPTC/DOOHC MIXTURES

The first step is the synthesis of HOPTC/DOOHC mixtures by the reaction in aqueous medium of maleate and D,L-tartrate reactants comprising both monovalent cation and calcium salts of maleic acid and D,L-Tartaric acid. As noted above, the total amount of maleate plus D,L-tartrate reactants in the aqueous reaction mixture will generally range from about 20% to about 70% by weight of the mixture, more preferably from about 55% to about 65% by weight. Calcium maleate is provided by first reacting maleic acid with calcium hydroxide or calcium carbonate the later preferably provided at least in part by recycle from earlier reactions. The D,L-tartrate is provided by hydroxylation of maleic acid (from maleic anhydride) in the presence of a catalyst and hydrogen peroxide by known means. One portion of the D,L-tartaric acid employed in the synthesis reaction is taken from the neutralized hydroxylation reaction product. Another portion of the needed D,L-tartrate is provided by the recycled calcium D,L-tartrate provided by earlier reactions as will be more fully described below.

The molar ratio of maleic acid to D,L-tartaric acid in the reaction mixture provided from all the sources noted above will generally range from about 0.5:1 to 8:1, more preferably from about 0.8:1 to about 1.2:1. The ratio of reactants will control the ratio of HOPTC/DOOHC in the final product.

As noted above the synthesis reaction takes place in the presence of a catalyst comprising calcium ions. To provide the necessary amount of calcium cation, several sources are used. Calcium maleate, prepared from recycled calcium carbonate and maleic acid provides one calcium ion source. Previously used but unreacted calcium D,L-tartrate recovered in the process of this invention provides another major calcium ion source. Any additional needed calcium ions usually a very small amount, can be provided by an additional calcium ion source such as calcium hydroxide added either as a solid or as a slurry. Other water soluble calcium salts can be employed, but calcium hydroxide possesses the additional advantage of supplying needed hydroxide ions. The total amount of calcium ion present provides a total molar ratio of calcium cation to maleate of 1:1. However, the amount of calcium cation can vary greatly and may be such that the ratio of moles of calcium cations to total moles of maleic and D,L-tartaric acids in solution can approach, but be less than 1.

The hydroxide of a monovalent cation is also essentially added to the reaction mixture as a source of alkalinity. This neutralizing agent is usually added in an amount such that the ratio of moles of monovalent cations to total moles of D,L-tartaric acid plus the moles of maleic acid minus the moles of calcium cations ranges from about 2.1:1 to about 3.8:1 More preferably this ratio ranges from about 2.2:1 to about 3.3:1. The monovalent cation-containing neutralizing agent can be any hydroxide which upon addition to water yields monovalent neutralizing cations in solution. Such neutralizing agents include, for example, alkali metal, ammonium or substituted ammonium hydroxide. Sodium hydroxide is highly preferred.

Sufficient neutralizing agent which, in combination with calcium hydroxide, is added to the synthesis reaction mixture to insure that the reaction mixture is overneutralized. Thus, the reaction mixture in the process of this invention will generally have a pH within the range of from about 8.5 to 13, more preferably from about 10.5 to about 12.5. The aqueous reaction mixture, after the appropriate amounts of reactants, catalysts and neutralizing agent are combined, is maintained at a temperature of from about 20° C. to about 120° C., preferably from about 70° C. to about 95° C. for a period of time sufficient to form a reaction product mixture containing the desired amounts of HOPTC and DOOHC. Reaction times of from about 0.5 to 50 hours, more preferably from about 1 to 4 hours, would generally be suitable for realizing acceptable yields of the 2 components of the desired mixture Reaction time is highly affected by temperature whereby higher temperature increases the rate of reaction.

At completion of the reaction the mixture is quenched with water to cool it to a temperature in the range of 80° C. Addition of water also improves the handling of the viscous reaction mass.

MONOSODIUM MALEATE AND D,L-TARTRATE PRECIPITATION

The reaction mixture containing mixed salts of HOPTC and DOOHC also contains relatively large amounts of unreacted maleic and tartrate acid salt. These salts are recovered and recycled to provide higher efficiency of utilization of this valuable raw material.

The recovery of these salts is achieved by a two step method of lowering of the pH of the reaction mixture whereby sodium hydrogen maleate or monosodium maleate and calcium tartrate precipitate. In the preferred embodiment the reaction mixture is cooled and diluted with water. An acidic material such as sulfuric acid, or an organic acid such as formic acid is combined with the reaction mixture in sufficient amount to bring the combined synthesis mass and acid to an initial pH in the range of from about 6.0 to about 9, preferably slightly below 7. Then, with further addition of suitable acid the pH of the reaction mixture is relatively more rapidly acidified further to a pH in the range of from about 4.5 to below 6, preferably to about 4.8 to about 5.2.

Any number of acidic materials can be employed to lower the pH of the reaction mixture. Combinations of acidic materials may also be employed. Typical examples of such acids are sulfuric acid, hydrochloric acid, nitric acid, formic, acetic, propionic, butyric and D,L-tartaric, carbonic, phosphoric, sulfonic, sulfurous, boric, phosphorous, adipic, benzoic, citric, fumaric, glycolic, malic, maleic, malonic, oxalic, succinic, sorbic, nitrilotriacetic, long chain fatty acids, etc.

In the process of this invention, the acid substance may be added to the crude reaction mass. Alternately, the reaction mass may be added to a heel containing the acid substance. In a further process of this invention, the acid substance and the reaction mass may be added concurrently into a mixing vessel. Sufficient water is added to the reaction mass and/or acid material so that the final concentration of desired ether carboxylate in the completed mixture is about 40%.

Sufficient acid is added to reach a preferred pH of near 5.0 and the precipitated reaction mass is cooled to below 50° C., preferably from just above the freezing point of the mixture to about 40° C. most practically to from about 20° C. to about 30° C. to obtain usable filtration rates in large scale production. In a preferred mode, cooling the reaction product from the 80° C. reaction temperature to 65° C. over 30 minutes is followed by slow cooling to from about 30° C. to about 40° C. The suspension is then allowed to rest for about 30 minutes. The slurry is preferably cooled slowly with mild or slow agitation so as to grow particles which can be filtered in an appropriately short time. Other methods of acid addition such as are noted above can also be employed with appropriate adjustment of precipitation conditions.

In the process of this invention wherein HOPTC and DOOHC are produced it has been found that both unreacted starting acids, D,L-tartaric acid and maleic acid can be recovered in their salt form. Also, it has been found that the calcium salt of D,L-tartaric acid precipitates from the reaction mixture at a pH in the range of from about 7 to about 12 and is typically of smaller crystal habit than the maleate salt. However, according to this invention the two acid salts may be precipitated in a two step procedure which produces globular particles including both acid salts.

When a mixed acid solution is employed to precipitate tartrate and maleate in the process of this invention, the acids may be added either sequentially or concurrently. In one mode of operation, the reaction mass at a temperature of about 80° C., is added to a heel of aqueous acid, typically formic acid, and then a solution of maleic acid is added to the partly neutralized reaction mass.

It has been found that when the pH of the reaction mixture is in the above-stated range calcium D,L-tartrate precipitates when such mixture is diluted with water or cooled to a temperature in the range of from about at least above freezing to about 70° C. The reaction mixture is typically diluted with water in amounts up to about 200 percent by weight. Greater dilution may be accomplished but additional amounts of water are not beneficial due to increased solubility or the salts being precipitated and also would probably require removal later. Dilution of the reaction mixture by about 30 to about 80 percent, by weight, is typical and usually both cooling and dilution are employed to provide maximum amount of tartrate precipitation.

In the process of this invention, there is employed, in conjunction with the above-noted stepwise reduction of pH, the use of crystal seeding whereby small particles of calcium tartrate/monosodium maleate recovered from previous production of mixtures of HOPTC and DOOHC are added to the reaction mixture. Thus, when the temperature of the reaction mixture is first reduced to about 80° C. by diluting the reaction mixture as noted above, crystals of calcium tartrate/sodium maleate from a previous batch are introduced into the reaction mixture. Amounts of crystals in the range of up to about 30 percent of the expected weight of the fresh precipitate may be added. When crystals are employed from the previous filter cake there is provided seed crystals of monosodium maleate. These crystals dissolve leaving calcium tartrate. However, the dissolved monosodium tartrate buffers the solution to a pH of about 6. When the pH is reduced in the second step dissolved monosodium maleate begins to precipitate below about 5.8.

Following the addition of crystals, the pH of the reaction mixture is then slowly reduced by combining the reaction mixture with acid to provide a reaction mixture having a pH in the range of about 7 to about 9 without prior seeding as described above. However, with seeding as noted above it is more preferable to reduce the pH of the reaction mixture in the first step of pH reduction to from about 6 to about 7. While lowering the pH of the reaction mixture it is also cooled to a temperature in the range of from above the freezing point of the mixture to about 50° C. It has been surprisingly found that, in the second step of pH reduction when the pH of the reaction mixture is reduced rapidly, or over a brief period of time, for example up to about one minute to about 10 minutes, unexpectedly large agglomerates of the combined salts of calcium tartrate and monosodium maleate are created. Throughout pH reduction, cooling is required to maintain the temperature of the reaction mixture in the desired range of from above freezing to about 35° C. As noted above, the reaction mixture is held for about 30 to about 40 minutes after final pH reduction to allow crystal formation. It is preferred to allow a short rest period between steps whereby the reaction mixture, at a pH above about 6, rests for about 10 minutes before the second step of pH reduction is performed. The larger agglomerates are more easily separated from the reaction mixture.

Removal of the precipitated acid salt may take any form practical and typically is performed by continuously drawing the slurry from the precipitator to a belt or drum filter or centrifuge. Other forms of removal such as decantation, etc. may also be employed. The filtrate contains the ether carboxylate in salt form. In a preferred embodiment the filtrate is transferred to another precipitator for removal of the calcium cations in the form of calcium carbonate.

In the production the HOPTC/DOOHC mixture filter cake is discharged and, in one embodiment, reslurried with water. The slurry is recycled directly or indirectly to the synthesis reactor to supply a portion of the required D,L-tartrate and maleate salts. Preferably the recovered maleate salt and/or D,L-tartrate salt is slurried with water and mixed with calcium maleate for recycle into the synthesis reaction.

CALCIUM CARBONATE PRECIPITATION

After removal of the insoluble acid salt or salts as described above, the filtrate from such operation is recovered and purified for use as detergent builder. In a preferred embodiment, calcium is removed either batchwise or preferably continuously. Typically, the filtrate from the above-mentioned step is pH adjusted with a base, preferably sodium hydroxide, as it is being fed into a calcium carbonate precipitator to bring the pH of the solution into a range of from about 10 to about 12, preferably from about 10 to about 10.5. The pH adjustment may be performed either in the precipitator or in a separate vessel if desired. The pH adjusted material is maintained in the range of from about 75° C. to about 110° C., preferably at about 90° C. to 100° C. Concurrently a solution of a basic carbonate, preferably sodium carbonate, preferably at a concentration of about 25%, is added to the precipitator to provide an overall mole ratio of carbonate to calcium of 1.3:1.

Alternatively, calcium carbonate is removed by increasing the mole ratio of carbonate ion to calcium ion without change in pH.

Although this invention is described with respect to carbonate precipitation using the preferred sodium cation, it is to be understood that other suitable cations may also be employed to obtain precipitation of calcium carbonate. Other cations useful in the process of this invention include potassium, ammonium or organo substituted ammonium. Other salts may be employed to obtain the calcium carbonate precipitate and includes sodium bicarbonate and mixtures of carbonates and bicarbonates.

During the precipitation of calcium carbonate it is preferred that water is continuously removed from the slurry to maintain the concentration of the organic acid salts in the range of from about 30% to about 50% by weight. Filtration of the precipitated calcium carbonate may take any form practical and typically is performed by continuously drawing the slurry from the precipitator to a centrifuge or to a belt or drum filter. The filtrate contains the desired ether carboxylate mostly as the alkaline salt along with minor amounts of raw material and by-products. In the preparation of HOPTC-/DOOHC mixtures, the by-products comprise typically less than 20% by weight of the HOPTC and DOOHC present.

The wet cake from the separation is mechanically reslurried with water to form an approximately 50% calcium carbonate slurry for recycle to the synthesis reaction. The recovered carbonate may be added directly to the ether carboxylate synthesis reactor or together with recovered, unreacted tartrate and maleate. Preferably, the recovered calcium carbonate is converted to calcium maleate in a separate vessel before return to the synthesis reaction.

CALCIUM MALEATE FORMATION

Before introduction into the synthesis reaction, the calcium carbonate precipitate obtained from the product as described above is preferably converted to calcium maleate by reaction with maleic acid. Preferably, the maleic acid is prepared in situ. In one embodiment, the maleic acid is prepared by charging molten maleic anhydride to water heated to 65° C. to 75° C. After hydrolysis of the maleic anhydride to maleic acid is complete, the slurry of calcium carbonate solids is added at a rate slow enough to avoid uncontrolled foaming due to the evolution of carbon dioxide. During the addition of calcium carbonate the reaction mass is heated to a temperature in the range of from about 90° C. to about 100° C. and preferably to about 95° C.

In the production of HOPTC and DOOHC it is preferred that calcium D,L-tartrate and monosodium maleate slurry obtained from the tartrate/maleate removal step is added to the calcium maleate while heating to a boil at atmospheric pressure. The mixture is held at boiling for about 15 minutes to ensure conversion of all of the calcium carbonate to the maleate. The mixture is then charged to the synthesis reactor for the preparation of additional HOPTC and DOOHC. During transfer to the synthesis reactor water may be evaporated to reduce volume.

Although the above described process follows a particular scheme, it is obvious that other schemes or flow charts may also be followed. For example, hold tanks, mixing tanks and transfer tanks may be employed which are not described above. Other variations will occur to those knowledgeable in the art.

EXTRACTION

The filtrate obtained from the procedure to remove calcium carbonate is purified by extraction with methanol and water. Such purification in the production of HOPTC and DOOHC mixtures is shown in U.S. Pat. No. 4,633,071 referred to above.

According to such patent the solution obtained after removal of calcium carbonate is thoroughly mixed with methanol. After settling, two layers form because the desired solution of HOPTC and DOOHC is less soluble in methanol than the impurities to be removed. The undesired solution is decanted and stripped of residual methanol. The residue is dissolved in water and extracted again with methanol.

After purification the product is concentrated so as to provide the desirable concentration of ether carboxylate solution for use as detergent builder or sequestrant. The concentrated material may also be dried by any typical means such as by spray drying, etc. to provide granular or particulate material which is the form traditionally employed.

To further illustrate the process of the present invention there is described below nonlimiting preferred embodiments. In the following examples all percentages are by weight unless otherwise noted.

EXAMPLE 1

Into a round bottom flask equipped with a thermometer, addition funnel, condenser and mechanical stirrer there were placed 39.4 g of maleic anhydride and 200 g of water. The mixture was heated to 70° C. to form maleic acid to which was added 50.1 g of calcium carbonate. Then wet filter cake, 350 g, from a previous run together with 100 g of water were added to the flask. The wet cake contained the following in weight percent:

Disodium meso tartrate—0.321
Calcium D,L-tartrate—19.62
Disodium Malate—1.27
HOPTC—13.24
DOOHC—0.7
Monosodium Fumarate—15.71

After addition of wet cake 62.95 g of D,L-tartaric acid and 550 g of disodium tartrate solution obtained by hydrolysis of epoxysuccinate were added to the reaction. This mixture was heated to 90° C. with stirring. Air was swept through the reactor to remove about 760 g of water during a period of 70 minutes after the reaction mass reached 90° C. Then 127.9 g of sodium hydroxide, 50% solution, was added to the mixture. Heating at 90° C. was continued for another 90 minutes. The reaction mixture was quenched with 126 g of water to reduce the organic solids content from 65% to 54% thereby cooling the reaction mass from 90° C. to about 80° C. The resulting mixture, a clear solution, was then divided into 2 parts with Portion A containing 566 g and Portion B containing 280 g.

A

Into this portion of the reaction mixture 40 g of filter cake from a previous reaction containing both calcium tartrate and sodium hydrogen maleate together with 160 g of water were added and the reaction mass held at 60° C. After holding for 10 minutes at that temperature formic acid was added over 20 minutes to lower the pH to 5.9. After reducing the pH the reaction mixture was cooled to 35° C. over 30 minutes. The reaction mixture was then held at 35° C. for an additional 30 minutes. A sample was taken for a filtration rate test (A-1). Then a 40% maleic acid solution was added to adjust the pH to 4.85 over a period of about 5 minutes and the system again held at 35° C. for an additional 30 minutes. Another sample was taken (A-2).

B

In this portion of the reaction mixture there were added 15 g of calcium tartrate filter cake as described above in Part A together with 80 g of water. The diluted reaction mixture was then cooled to 35° C. Then formic acid was added over a period of 20 minutes to adjust the pH to 6. The reaction mixture at the lower pH value was held at 35° C. for 45 minutes and a sample taken for a filtration rate test (B-1). A 40% maleic acid solution was added to adjust the pH to 4.8 with relatively rapid addition and the system held at 35° C. for an additional 30 minutes. Another sample was taken for a filtration rate test (B-2). The results of these tests are presented below in Table I. As shown in Table 1, the filtration rates of both samples in Part B are much lower than the samples in Part A. This is believed to be due to the addition of greater amounts of crystal seed material from the previous filter cake in Part A. The filtration rate reported in Table I below was measured at a cake thickness of 12.7 mm.

TABLE I

| Sample | A-1 | A-2 | B-1 | B-2 |
|---|---|---|---|---|
| pH during filtration | 5.9 | 4.85 | 6.0 | 4.8 |
| Filtration rate liters/hr/meter$^2$ | 4237 | 11,407 | 1263 | 3259 |

The filtrates were analyzed to determine their components. The results of the analyses are shown in Table II below. The results indicate that the maleate salt is mostly removed from the system at the lower pH even though maleic acid is employed to acidify the reaction mixture.

TABLE II

| Analyses | A-1 | A-2 | B-1 | B-2 |
|---|---|---|---|---|
| Disodium tartrate | 2.2 | 1.9 | 2.0 | 1.6 |
| Disodium malate | 0.3 | 0.3 | 0.0 | 0.0 |
| Disodium maleate | 4.6 | 0.7 | 4.3 | 0.5 |
| Disodium fumarate | 1.1 | 1.2 | 1.1 | 1.0 |
| HOPTC | 21.0 | 21.5 | 20.4 | 20.0 |
| DOOHC | 3.2 | 3.3 | 3.1 | 3.3 |

EXAMPLE 2

This example demonstrates the disadvantage of cooling the reaction mixture before reducing the pH by combining their mixture with acid. A reaction mixture obtained in accordance with the procedure of Example 1 was obtained and divided into four equal portions of 180 g, then each was quenched with 40 g of water. A heel comprising 10 g of formic acid, 88%, and 40 g of water was prepared for each portion.

A

One portion of the reaction mixture at 52° C. was added to the acid heel thereby lowering the pH of the mixture to about 6.9 while cooling continued over a period of about 32 minutes. Cooling was then continued until the reaction mixture and the combined heel reached about 34° C. The maleic acid mixture, 40%, was then added over a period of about 5 minutes with continued cooling to maintain the reaction mixture at about 34° C. and lowering the pH to 5.0. Globular precipitate formed and the mixture was then filtered to recover the precipitate.

B

The reaction mixture was cooled to 43° C. before being added to the heel. The combined heel and reaction mixture was further cooled to a temperature of about 30° C. during combination which produced a pH of 7.05 after holding at the noted temperature and pH for about 10 minutes. Maleic acid was then added to the solution over a period of 6 minutes lowering the pH to 5.0. The resulting mixture was then filtered to recover the precipitate.

The filtration rate of each precipitate was measured during filtration and the results appear in Table III below.

TABLE III

| | Filtration Rate - liters/hr/M$^2$ | |
|---|---|---|
| Cake Thickness - mm | A | B |
| 9.5 | 2770.3 | 1751.8 |
| 12.7 | 2077.7 | 1495.1 |
| 15.8 | 1670.7 | 1197.7 |

The data in Table III above indicates that combining the reaction mixture with the acid heel at higher temperature improves the filtration rates.

EXAMPLE 3

A reaction mixture obtained in accordance with the procedure of Example 1, 360 g, was quenched with 80 g of water and cooled to about 80° C. An acid heel was prepared by combining 23 g of 88% formic acid and 80 g of water. Into this heel was charged the quenched reaction mixture; however, the pH was lowered, with cooling to about 35° C. as it was combined with the acid heel in the one step whereby the pH of the combination reached about 6.3. Maleic acid, 40%, was added over a period of one hour resulting in a final pH of 5.0. Cooling continued for an additional one hour and 40 minutes to obtain a final temperature of 32° C. The precipitate was recovered by filtration and the filtration rates at the varying filter cake thicknesses are reported below.

TABLE IV

| Cake Thickness - mm | Filtration Rate - liters/hr/M$^2$ |
|---|---|
| 9.5 | 1222.2 |
| 12.7 | 937 |
| 15.8 | 774 |

By comparing the data presented in Tables III and IV the improvement in filtration rate in accordance with this invention is clearly shown.

There has been described a novel process of general application for the production of ether carboxylates. While the process has been described with reference to specific compounds no intention is made by such reference to limit the scope of this invention unless expressly stated. Various modifications may be made in the materials and sequence of process steps as well as process combinations which are adapted to suit the various reactants and products without departing from this invention.

I claim:

1. In a process for preparing mixtures of 1-hydroxy-3-oxa-1,2,4,5-pentane tetracarboxylic acid and 3,6-dioxa-1,2,4,5,7,8-octane hexacarboxylic acid which comprises reacting in an alkaline reaction medium the salts of maleic acid and tartaric acid in the presence of calcium ion catalyst, wherein the pH of the reaction product is reduced to a range of from about 4 to below 6, the improvement comprising reducing the pH in two steps wherein in the first step the pH is reduced to a pH of from about above 6 to about 9 an din the second step the pH is reduced at a more rapid rate than in said first step whereby unreacted starting acids are precipitated in particles of a size which provide increased porosity and filter rate, recovering said acids from the reaction product.

2. The process of claim 1 wherein the temperature of the reaction product is cooled to a temperature in the range of from above freezing to about 50° C. during reduction in pH.

3. The process of claim 1 wherein the second step of pH reduction is delayed for a period of about 10 minutes after completion of the first step.

4. The process of claim 1 wherein the pH of the reaction product at the end of the first step is in the range of from about 6.0 to about 7.0.

5. The process of claim 4 wherein the pH of the reaction product at the end of the second step of pH reduction is in the range of about 4.8 to about 5.2.

6. The process of claim 1 wherein the pH is reduced in the first step by adding the reaction product to a heel containing acid.

7. The process of claim 6 wherein the pH of the reaction product is reduced by addition of maleic acid.

8. A process of claim 1 wherein the pH is reduced by combining the reaction product with an organic acid.

9. A process of claim 8 wherein the organic acid is selected from the group consisting of formic, acetic, propionic, citric, maleic, tartaric, fumaric, malic, malonic, succinic, adipic, butyric and long chain fatty acids.

10. A process of claim 1 wherein the pH is reduced by combining the reaction product with an inorganic acid.

11. A process of claim 10 wherein the inorganic acid is selected from the group consisting of sulfuric, hydrochloric, carbonic, nitric, phosphoric, phosphorous, sulfonic and sulfurous acids.

12. A process of claim 1 wherein the pH is reduced by combining the reaction product with a mixture of organic and inorganic acid.

13. A process of claim 12 wherein the acids are sulfuric and maleic acids.

14. A process of claim 12 wherein acid heel contains a mixture of two acids.

15. A process of claim 14 wherein the acids in the heel are formic and maleic.

16. A process of claim 1 further including the step of reducing the amount of calcium in the reaction product after removal of the unreacted starting acids by means of increasing the pH of the remaining solution to within a range of from about 7 to about 12 and combining the reaction product with a basic carbonate whereby calcium carbonate precipitates and is removed from the reaction product.

17. A process of claim 16 wherein the basic carbonate is sodium carbonate.

18. A process for preparing a mixture of the alkali metal salt of 1-hydroxy-3-oxa-1,2,4,5-pentane tetracarboxylic acid and 3,6-dioxa-1,2,4,5,7,8-octane hexacarboxylic acid which comprises the steps of:
 (a) forming an aqueous reaction mixture comprising from about 20% to 60% by weight of both calcium and monovalent cation salts of maleic acid and tartaric acid, said mixture corresponding to the over-neutralized mixture which is formed by combining:
  (i) maleic and tartaric acids in a maleic to tartaric molar ratio of from about 0:5:1 to about 8:1;
  (ii) a source of calcium cations in an amount such that the molar ratio of calcium to tartaric acid ranges from about 0.1:1 to 2.0:1 with the ratio of moles of calcium to total moles of maleic and tartaric acid being less than 1; and
  (iii) a neutralizing agent comprising a hydroxide of a monovalent cation in an amount such that the ratio of moles of monovalent cation to moles of maleic acid plus moles of tartaric acid minus moles of calcium ranges from about 2.1:1 to 3.8:1.
 (b) maintaining said aqueous reaction mixture at a temperature of from about 20° C. to 120° C. for a time period sufficient to form a reaction product mixture of said 1-hydroxy-3-oxa-1,2,4,5-pentane tetracarboxylic acid salts and 3,6-dioxa-1,2,4,5,7,8-octane hexacarboxylic acid salts;
 (c) lowering the pH of reaction mixture of step (b) to the range of from about 4.5 to about 5.5 and cooling the mixture to precipitate calcium tartrate and monosodium maleate in two steps wherein the pH is first reduced to a range of from about 6 to about 9 then lowering the pH more rapidly than in said first step whereby unreacted starting acids are precipitated in particles of a size which provides increased porosity and filter rate;
 (d) removing the precipitate from the reaction mixture formed in step (c) and recycling it to step (a) to prepare additional amounts of reaction product;
 (e) treating the reaction mixture from step (d) with a carbonate or bicarbonate whereby calcium carbonate precipitates;
 (f) removing the calcium carbonate from the reaction mixture of step (e) and recycling it to step (a) to prepare additional amounts of reaction product; and
 (g) recovering and purifying the reaction mixture from step (f).

19. A process of claim 18 wherein the pH of the filtrate of step (d) is in the range of from 9 to 11 before combining with the carbonate.

20. A process of claim 18 wherein the mole ratio of carbonate to calcium in step (d) is 1.3:1.0.

21. A process of claim 18 wherein the neutralizing agent is sodium hydroxide.

22. In a process for preparing mixtures of 1-hydroxy-3-oxa-1,2,4,5-pentane tetracarboxylic acid and 3,6-dioxa-1,2,4,5,7,8-octane hexacarboxylic acid which comprises reacting in an alkaline reaction medium the salts of maleic acid and tartaric acid in the presence of calcium ion catalyst, wherein the ph of the reaction product is reduced to a range of from about 4 to below 6 the improvement comprising reducing the pH in two steps wherein in the first step the pH is reduced to a pH of from about 6 to about 9 an din the second step the pH is reduced at a more rapid rate than in said first step whereby unreacted starting acids are precipitated in particles of a size which provide increased porosity and filter rate, recovering said acids from the reaction product, then increasing the pH of the remainder of the reaction mixture by addition of a carbonate or bicarbonate whereby calcium carbonate precipitates and is removed from the reaction mixture and reacting said calcium carbonate with maleic acid to form a calcium salt of said acid for use in said process.

23. A process for preparing a mixture of the alkali metal salt of 1-hydroxy-3-oxa-1,2,4,5-pentane tetracarboxylic acid and 3,6-dioxa-1,2,4,5,7,8-octane hexacarboxylic acid which comprises the steps of:

(a) forming an aqueous reaction mixture comprising from about 20% to 60% by weight of both calcium and monovalent cation salts of maleic acid and tartaric acid, said mixture corresponding to the over-neutralized mixture which is formed by combining:
  (i) maleic and tartaric acids in a maleic to tartaric molar ratio of from 0.5:1 to about 8:1;
  (ii) a source of calcium cations in an amount such that the molar ratio of calcium to tartaric acid ranges from about 0.1:1 to 2.0:1 with the ratio of moles of calcium to total moles of maleic and tartaric acid being less than 1; and
  (iii) a neutralizing agent comprising a hydroxide of a monovalent cation in an amount such that the ratio of moles of monovalent cation to moles of maleic acid plus moles of tartaric acid minus moles of calcium ranges from about 2.1:1 to 3.8:1.

(b) maintaining said aqueous reaction mixture at a temperature of from about 20° C. to 120° C. for a time period sufficient to form a reaction product mixture of said 1-hydroxy-3-oxa-1,2,4,5-pentane tetracarboxylic acid salts and 3,6-dioxa-1,2,4,5,7,8-octane hexacarboxylic acid salts;

(c) lowering the pH of reaction mixture of step (b) to the range of from about 4.5 to about 5.5 and cooling the mixture to precipitate calcium tartrate and monosodium maleate in two steps wherein the pH is first reduced to a range of from about above 6 to about 9 and then lowering the pH more rapidly than in said first step whereby unreacted starting acids are precipitated in particles of a size which provides increased porosity and filter rate;

(d) removing the precipitate from the reaction mixture formed in step (c), then reacting said precipitate with calcium carbonate and sufficient maleic acide to convert the monosodium maleate to calcium maleate and employing said maleate in step (a);

(e) treating the reaction mixture from step (d) with a carbonate or bicarbonate whereby calcium carbonate precipitates;

(f) removing the calcium carbonate from the reaction mixture of step (e) and reacting said carbonate with maleic acid to form a calcium salt of maleic acid;

(g) employing said calcium salt of maleic acid to prepare additional ether carboxylates in step (a) above; and (h) recovering and purifying the reaction mixture from step (f).

24. A process of claim 23 wherein the carbonate is an alkali metal carbonate.

25. A process of claim 24 wherein the alkali metal is sodium.

26. A process of claim 24 wherein the bicarbonate is sodium bicarbonate.

* * * * *